United States Patent [19]
Thomas et al.

[11] Patent Number: 5,959,175
[45] Date of Patent: Sep. 28, 1999

[54] SUNFLOWER ALBUMIN 5' REGULATORY REGION FOR THE MODIFICATION OF PLANT SEED LIPID COMPOSITION

[76] Inventors: Terry L. Thomas, 2804 Cloister Dr., College Station, Tex. 77845; Andrew N. Nunberg, 12215-B Encanto La., Maryland Heights, Mo. 63043; Phillip D. Beremand, 9208 Brookwater Cir., College Station, Tex. 77845

[21] Appl. No.: 08/831,570

[22] Filed: Apr. 9, 1997

[51] Int. Cl.$^6$ .............................. A01H 5/00; A01H 5/10; C12N 15/29; C12N 15/82; C12P 7/64

[52] U.S. Cl. ..................... 800/287; 800/281; 800/286; 800/306; 800/312; 800/314; 800/317.3; 800/320.1; 800/322; 435/69.1; 435/134; 435/252.3; 435/320.1; 435/419; 435/468; 536/23.6; 536/24.1; 536/24.5

[58] Field of Search .......................... 435/69.1, 172.3, 435/320.1, 419, 468, 252.3, 134; 536/24.1, 23.6, 24.5; 800/205, DIG. 14, DIG. 15, DIG. 17, DIG. 26, DIG. 27, DIG. 43, DIG. 56, DIG. 69, 287, 286, 281, 306, 312, 314, 317.3, 320.1, 322

[56] References Cited

U.S. PATENT DOCUMENTS

| | | | |
|---|---|---|---|
| 5,365,015 | 11/1994 | Grierson et al. | 800/205 |
| 5,552,306 | 9/1996 | Thomas et al. | 435/134 |
| 5,614,393 | 3/1997 | Thomas et al. | 435/134 |

FOREIGN PATENT DOCUMENTS

| | | |
|---|---|---|
| WO 91 13972 | 9/1991 | WIPO . |
| WO 92 11373 | 7/1992 | WIPO . |
| WO 92 17580 | 10/1992 | WIPO . |
| WO 93 11245 | 6/1993 | WIPO . |
| WO 94 10189 | 5/1994 | WIPO . |
| WO 94 11516 | 5/1994 | WIPO . |
| WO 94 18337 | 8/1994 | WIPO . |
| WO 96 06936 | 3/1996 | WIPO . |
| WO 96 21022 | 7/1996 | WIPO . |

OTHER PUBLICATIONS

Smith et al. Antisense RNA inhibition of polygalacturonase gene expression in transgenic tomatoes. Nature. 334:724–726, Aug. 1988.

Napoli et al. Introduction of a chimeric chalcone synthase gene into petunia results in reversible co–suppression of homologous genes in trans. The Plant Cell. 2:270–289, Apr. 1990.

Allen et al. Sequence and expression of a gene encoding an albumin storage protein in sunflower. Molecular General Genetics. 210:211–218, Dec. 1987.

Reddy et al. Isolation of a delta–6–desaturase gene from the cyanobacterium Synechocystis sp. strain PCC 6803 by gain–of–function expression in Anabaena sp. strain PCC 7120. Plant Molecular Biology. 27:293–300, May 1993.

Reddy et al. Expression of a Cyanobacterial delta–6–desaturase gene results in a gamma–linolenic acid production in transgenic plants. Nature Biotechnology. 14;639–642, May 1996.

Kim et al. A 20 nucleotide upstream element is essential for the nopaline synthase (nos) promoter activity. Plant Molecular Biology. 24;105–117, 1994.

Allen, et al. (1987) "Sequence and Expression of a Gene Encoding An Albumin Storage Protein in Sunflower", *Mol. Gen. Genet.*, 210:211–218.

Beremand, P.D., et al. (1997) "Production of gamma–linolenic acid by transgenic plants expressing cyanobacterial or plant delta6–desaturase genes", *Proc. Int. Symp. Plant Lipids*, 12th: 351–353.

Töpfer, et al. (1995) "Modification of Plant Lipid Synthesis", *Science*, 268:681–686.

Gibson, S., et al. (1994) "Cloning of a temperature–regulated gene encoding a chloroplast omega–3 desaturase from *Arabidopsis thaliana*", *Plant Physiology*, 104: 1615–1621.

Allen, et al. (1985) "Developmental Expression of Sunflower 11S Storage Protein Genes", *Plant Molecular Biology*, 5:165–173.

Brenner, R.R. (1976) "Regulatory Function of Δ6 Desaturase—Key Enzyme of Polyunsaturated Fatty Acid Synthesis", *Adv. Exp. Med. Biol.*, 83:85–101.

Cahoon, et al. (1992) "Expression of a Coriander Desaturase Results in Petroselinic Acid Production in Transgenic Tobacco", *Proc. Natl. Acad. Sci USA*, 89:11184–11188.

Crouch, et al. (1983) "cDNA Clones for *Brassica napus* Seed Storage Proteins: Evidence from Nucleotide Sequence Analysis that Both Subunits of Napin are Cleaved from a Precursor Polypeptide", *J. Mol. Appl. Genet.*, 2:273–284.

Ericson, et al. (1986) "Structure of the Rapeseed 1.7 S Storage Protein, Napin, and Its Precursor", *J. Biol. Chem.*, 261:14576–14581.

Higgins, et al. (1986) "Gene Structure, Protein Structure, and Regulation of the Synthesis of a Sulfur–rich Protein in Pea Seeds", *J. Biol. Chem*, 261:11124–11130.

Higgins, et al. (1987) "cDNA and Protein Sequence of a Major Pea Seed Albumin (PA 2:$M_r$~26 000)", *Plant Mol. Biol.*, 8:37–45.

Laroche–Raynal, et al. (1986) Identification and Characterization of the mRNA for Major Storage Proteins from Radish, *Eur. J. Biochem.*, 157:321–327.

Ohlrogge, et al. (1991) "The Genetics of Plant Lipids", *Biochim. et Biophys. Acta*, 1082:1–26.

(List continued on next page.)

*Primary Examiner*—David T. Fox
*Attorney, Agent, or Firm*—Scully, Scott, Murphy & Presser

[57] ABSTRACT

The present invention is directed to 5' regulatory regions of a sunflower albumin gene. The 5' regulatory regions, when operably linked to either the coding sequence of a heterologous gene or a sequence complementary to a native plant gene direct expression of the coding sequence or complementary sequence in a plant seed. The regulatory regions are useful in expression cassettes and expression vectors for the transformation of plants.

Also provided are methods of modulating the levels of a heterologous gene or native plant gene such as a fatty acid synthesis or lipid metabolism gene by transforming a plant with the subject expression cassettes and expression vectors.

28 Claims, 8 Drawing Sheets

OTHER PUBLICATIONS

Ohlrogge, J.B. (1994) "Design of New Plant Products: Engineering of Fatty Acid Metabolism", *Plant Physiol.*, 104:821–826.

Reddy, et al. (1996) "Expression of a Cyanobacterial Δ6–Desaturase Gene Results in a γ–Linolenic Acid Production in Transgenic Plants", *Nature Biotech.*, 14:639–642.

Sun, et al. (1987) "Properties, Biosynthesis and Processing of a Sulfur–Rich Protein in a Brazil Nut (*Bertholletia excelsa* H.B.K.)", *Eur. J. Bioch.*, 162:477–483.

Van de Loo, et al. (1995) "An Oleate 12–Hydroxylase from *Ricinus communis* L. is a Fatty Acyl Desaturase homolog", *Proc. Natl. Acad. Sci USA*, 92:6743–6747.

Weete, J.D. (1980) "Lipid Biochemistry of Fungi and Other Organisms", eds. Plenum Press, New York, pp. 59–62.

Youle et al. (1981) "Occurrence of Low Molecular Weight and High Cysteine Containing Albumin Storage Proteins in Oilseeds of Diverse Species", *Amer. J. Bot.*, 68:44–48.

```
2
ata tct gcc tac cct ccc aaa gag agt agt cat ttt tca tca atg gct gct caa atc aag
                                                         M   A   A   Q   I   K
62
aaa tac att acc tca gat gaa ctc aag aac cac gat aaa ccc gga gat cta tgg atc tcg
 K   Y   I   T   S   D   E   L   K   N   H   D   K   P   G   D   L   W   I   S
122
att caa ggg aaa gcc tat gat gtt tcg gat tgg gtg aaa gac cat cca ggt ggc agc ttt
 I   Q   G   K   A   Y   D   V   S   D   W   V   K  |D   H   P   G   G| S   F
182
ccc ttg aag agt ctt gct ggt caa gag gta act gat gca ttt gtt gca ttc cat cct gcc
 P   L   K   S   L   A   G   Q   E   V   T   D   A   F   V   A   F   H   P   A
242
tct aca tgg aag aat ctt gat aag ttt ttc act ggg tat tat ctt aaa gat tac tct gtt
 S   T   W   K   N   L   D   K   F   F   T   G   Y   Y   L   K   D   Y   S   V
302
tct gag gtt tct aaa gat tat agg aag ctt gtg ttt gag ttt tct aaa atg ggt ttg tat
 S   E   V   S   K   D   Y   R   K   L   V   F   E   F   S   K   M   G   L   Y
362
gac aaa aaa ggt cat att atg ttt gca act ttg tgc ttt ata gca atg ctg ttt gct atg
 D   K   K   G   H   I   M   F   A   T   L   C   F   I   A   M   L   F   A   M
422
agt gtt tat ggg gtt ttg ttt tgt gag ggt gtt ttg gta cat ttg ttt tct ggg tgt ttg
 S   V   Y   G   V   L   F   C   E   G   V   L   V   H   L   F   S   G   C   L
482
atg ggg ttt ctt tgg att cag agt ggt tgg att gga cat gat gct ggg cat tat atg gta
 M   G   F   L   W   I   Q   S   G   H   I   G   H   D   A   G   H   Y   M   V
542
gtg tct gat tca agg ctt aat aag ttt atg ggt att ttt gct gca aat tgt ctt tca gga
 V   S   D   S   R   L   N   K   F   M   G   I   F   A   A   N   C   L   S   G
602
ata agt att ggt tgg tgg aaa tgg aac cat aat gca cat cac att gcc tgt aat agc ctt
 I   S   I   G   W   W   K   W   N   H   N   A   H   H   I   A   C   N   S   L
662
gaa tat gac cct gat tta caa tat ata cca ttc ctt gtt gtg tct tcc aag ttt ttt ggt
 E   Y   D   P   D   L   Q   Y   I   P   F   L   V   V   S   S   K   F   F   G
722
tca ctc acc tct cat ttc tat gag aaa agg ttg act ttt gac tct tta tca aga ttc ttt
 S   L   T   S   H   F   Y   E   K   R   L   T   F   D   S   L   S   R   F   F
782
gta agt tat caa cat tgg aca ttt tac cct att atg tgt gct gct agg ctc aat atg tat
 V   S   Y   Q   H   W   T   F   Y   P   I   M   C   A   A   R   L   N   M   Y
A ─── · ─── · ─── · ─── · ─── · ─── · ─── ·─── A
```

```
842
gta caa tct ctc ata atg ttg ttg acc aag aga aat gtg tcc tat cga gct cag gaa ctc
 V   Q   S   L   I   M   L   L   T   K   R   N   V   S   Y   R   A   Q   E   L
902
ttg gga tgc cta gtg ttc tcg att tgg tac ccg ttg ctt gtt tct tgt ttg cct aat tgg
 L   G   C   L   V   F   S   I   W   Y   P   L   L   V   S   C   L   P   N   W
962
ggt gaa aga att atg ttt gtt att gca agt tta tca gtg act gga atg caa caa gtt cag
 G   E   R   I   M   F   V   I   A   S   L   S   V   T   G   M   Q   Q   V   Q
1022
ttc tcc ttg aac cac ttc tct tca agt gtt tat gtt gga aag cct aaa ggg aat aat tgg
 F   S   L   N   H   F   S   S   S   V   Y   V   G   K   P   K   G   N   N   W
1082
ttt gag aaa caa acg gat ggg aca ctt gac att tct tgt cct cct tgg atg gat tgg ttt
 F   E   K   Q   T   D   G   T   L   D   I   S   C   P   P   W   M   D   W   F
1142
cat ggt gga ttg caa ttc caa att gag cat cat ttg ttt ccc aag atg cct aga tgc aac
 H   G   G   L   Q   F   Q   I   E   H   H   L   F   P   K   M   P   R   C   N
1202
ctt agg aaa atc tcg ccc tac gtg atc gag tta tgc aag aaa cat aat ttg cct tac aat
 L   R   K   I   S   P   Y   V   I   E   L   C   K   K   H   N   L   P   Y   N
1262
tat gca tct ttc tcc aag gcc aat gaa atg aca ctc aga aca ttg agg aac aca gca ttg
 Y   A   S   F   S   K   A   N   E   M   T   L   R   T   L   R   N   T   A   L
1322
cag gct agg gat ata acc aag ccg ctc ccg aag aat ttg gta tgg gaa gct ctt cac act
 Q   A   R   D   I   T   K   P   L   P   K   N   L   V   W   E   A   L   H   T
1382
cat ggt taa aat tac cct tag ttc atg taa taa ttt gag att atg tat ctc cta tgt ttg
 H   G   *
1442
tgt ctt gtc ttg gtt cta ctt gtt gga gtc att gca act tgt ctt tta tgg ttt att aga
1502
tgt ttt tta ata tat ttt aga ggt ttt gct ttc atc tcc att att gat gaa taa gga gtt
1562
gca tat tgt caa ttg ttg tgc tca ata tct gat att ttg gaa tgt act ttg tac cac tgt
1622
gtt ttc agt tga agc tca tgt gta ctt cta tag act ttg ttt aaa tgg tta tgt cat gtt
1682
att t
```

FIG.IB

```
GAATTCTATC ACTAGTGACC ACCCCATCCC CTTATTTCAA TAATGGAACA  -811
CAAAAAAAAT TTTAAAAAAT AGTTGCTGTT AATTGTTTAA CCGTCATTTT  -761
CCAACATTAC TAGCTAATCG TTAATTGATC TTCATAAAAA AAAAAATTGC  -711
TATGGGTACT ATTGAGATTG TATATCTTAT CAGTTAGGCC TAAGGGGGGG  -661
GTCAGTGATA TTACGAATGA TACAAACATC AACGCGTGGA ACATTACAAA  -611
TTCCTATCCC CACCTCCAAG TATAACGCGT GTTTGTTCCA CGGTTTGATG  -561
ATTCCGTAAT TTTTTCAACG CCGTGATGGT TTTTTTTTTT TTTTTTTTTT  -511
TTGATGGTAA TTGTTGGTTG GGGGGAAATT ATTGGGTATG GTGTTGAGTG  -461
ATGACCACCC CCACTAAAAA AGGTTGTGAG TGATGTAAAA ATGGTTGCTG  -411
ACATGACGAA ACATAATTGG ATATTGTGAG TGATAAAATT TTATCATTAG  -361
TGACCACCCC GCCTCCCTT  ATCATATGTT GTTATCTTCC ATAGTTGCGG  -311
TATACCAACA TATGGTAGTT TTTATATTTA TAGTTTATAT TTTCATTAAA  -261
CTCTCTTCGC CAGGCTACTT GTATTGTAAT CATATGGAAT CTCAACTCCA  -211
CTTGGAGCCA TTCCATCATA TATTTCCATT TCCAAACAAA GAGAATTGAC  -161
ACCTCATACA TACTCCAAAG CATACTTCCA CTTGCTATAA TTTTCATGTA  -111
AAAACTCGTA CGTGTTATTC GACAATGTTC ATATAACGCC ACCGATTAAA   -61
CTCACCTCTC CACGTATGAA CCTCCACCCA CCATATATAC GCACCACCAC   -11
CACACCATAA TTCACACAAC CACAACACCA TCTCCCACAG GATCC        +29
```

FIG. 4

SUNFLOWER ALBUMIN 5' REGULATORY REGION FOR THE MODIFICATION OF PLANT SEED LIPID COMPOSITION

BACKGROUND OF THE INVENTION

Seed oil content has traditionally been modified by plant breeding. The use of recombinant DNA technology to alter seed oil composition can accelerate this process and in some cases alter seed oils in a way that cannot be accomplished by breeding alone. The oil composition of Brassica has been significantly altered by modifying the expression of a number of lipid metabolism genes. Such manipulations of seed oil composition have focused on altering the proportion of endogenous component fatty acids. For example, antisense repression of the Δ12-desaturase gene in transgenic rapeseed has resulted in an increase in oleic acid of up to 83%. Topfer et al. 1995 *Science* 268:681–686.

There have been some successful attempts at modifying the composition of seed oil in transgenic plants by introducing new genes that allow the production of a fatty acid that the host plants were not previously capable of synthesizing. Van de Loo, et al. (1995 *Proc. Natl. Acad. Sci USA* 92:6743–6747) have been able to introduce a Δ12-hydroxylase gene into transgenic tobacco, resulting in the introduction of a novel fatty acid, ricinoleic acid, into its seed oil. The reported accumulation was modest from plants carrying constructs in which transcription of the hydroxylase gene was under the control of the cauliflower mosaic virus (CaMV) 35S promoter. Similarly, tobacco plants have been engineered to produce low levels of petroselinic acid by expression of an acyl-ACP desaturase from coriander (Cahoon et al. 1992 *Proc. Natl. Acad. Sci USA* 89:11184–11188).

The long chain fatty acids (C18 and larger), have significant economic value both as nutritionally and medically important foods and as industrial commodities (Ohlrogge, J. B. 1994 *Plant Physiol.* 104:821–826). Linoleic (18:2 Δ9,12) and α-linolenic acid (18:3 Δ9,12,15) are essential fatty acids found in many seed oils. The levels of these fatty-acids have been manipulated in oil seed crops through breeding and biotechnology (Ohlrogge, et al. 1991 *Biochim. Biophys. Acta* 1082:1–26; Topfer et al. 1995 *Science* 268:681–686). Additionally, the production of novel fatty acids in seed oils can be of considerable use in both human health and industrial applications.

Consumption of plant oils rich in γ-linolenic acid (GLA) (18:3 Δ6,9,12) is thought to alleviate hypercholesterolemia and other related clinical disorders which correlate with susceptibility to coronary heart disease (Brenner R. R. 1976 *Adv. Exp. Med. Biol.* 83:85–101). The therapeutic benefits of dietary GLA may result from its role as a precursor to prostaglandin synthesis (Weete, J. D. 1980 in *Lipid Biochemistry of Fungi and Other Organisms*, eds. Plenum Press, New York, pp. 59–62). Linoleic acid(18:2) (LA) is transformed into gamma linolenic acid (18:3) (GLA) by the enzyme Δ6-desaturase.

Few seed oils contain GLA despite high contents of the precursor linoleic acid. This is due to the absence of Δ6-desaturase activity in most plants. For example, only borage (*Borago officinalis*), evening primrose (*Oenothera biennis*), and currants (*Ribes nigrum*) produce appreciable amounts of linolenic acid. Of these three species, only Oenothera and borage are cultivated as a commercial source for GLA. It would be beneficial if agronomic seed oils could be engineered to produce GLA in significant quantities by introducing a heterologous Δ6-desaturase gene. It would also be beneficial if other expression products associated with fatty acid synthesis and lipid metabolism could be produced in plants at high enough levels so that commercial production of a particular expression product becomes feasible.

As disclosed in U.S. Pat. No. 5,552,306, a cyanobacterial Δ$^6$-desaturase gene has been recently isolated. Expression of this cyanobacterial gene in transgenic tobacco resulted in significant but low level GLA accumulation. (Reddy et al. 1996 *Nature Biotech.* 14:639–642). Applicant's copending U.S. application Ser. No. 08,366,779, discloses a Δ6-desaturase gene isolated from the plant *Borago officinalis* and its expression in tobacco under the control of the CaMV 35S promoter. Such expression resulted in significant but low level GLA and octadecatetraenoic acid (ODTA or OTA) accumulation in seeds. Thus, a need exists for a promoter which functions in plants and which consistently directs high level expression of lipid metabolism genes in transgenic plant seeds.

Sunflower embryos accumulate two major classes of storage proteins. These are the 11S globulins, soluble in 1M NaCl, and 2S albumins, soluble in water (Youle et al. 1981 *Am J. Bot* 68:44–48). The synthesis, processing and accumulation of 2 S albumin seed proteins have been studied intensively in *Brassica napus* (Crouch et al., 1983 *J. Mol. Appl. Genet.* 2:273–284; Ericson et al., 1986 *J. Biol. Chem.* 261:14576–14581), pea (Higgins et al., 1986 *Plant Mol. Biol.* 8:37–45), radish (Laroche-Raynal et al., 1986 *Eur. J. Biochem.* 157:321–327), castor bean (Lord J. M., 1985 *Eur. J. Biochem* 146:403–409) and Brazil nut (Sun et al., 1987 *Eur. J. Biochem* 162:477–483). A major conclusion of these studies is that the characteristic low molecular weight, disulfide-linked albumin polypeptides found in mature seeds result from the extensive processing of larger precursors synthesized during embryogenesis. Two additional characteristics that define the 2S albumin seed storage proteins are high amide content and high frequency of cysteine residues (Youle et al., 1981).

In sunflower, the 2S albumins represent more than 50% of the protein present in seeds (Youle et al., 1981) and consist of two or three closely related polypeptides with molecular weights of approximately 19 kDa (Cohen, E. A., 1986 "Analysis of sunflower 2S seed storage protein genes" MS thesis, Texas A&M University; Allen et al. 1987 *Plant Mol Biol* 5:165–173). The sunflower albumin is apparently maintained in a compact structure by intramolecular disulfide bonds resulting in a rapidly migrating species with an apparent molecular weight of 14 kDa when analyzed by SDS-polyacrylamide gel electrophoresis (SDS-PAGE) under non-reducing conditions. When reduced, this species migrates as a 19 kDa polypeptide (Cohen, E. A., 1986). In contrast, most other 2S proteins are composed of large and small subunit polypeptides, derived from a single precursor, and linked by itnermoleclar disulfide bonds (Crouch et al. 1983 *J. Mol. Appl. Genet.* 2:273–284; Ericson et al. 1986 *J. Biol. Chem.* 261:14576–14581; Sun et al. 1987, *Eur. J. Bioch.* 162:477–483. )

Albumin polypeptides can be detected in sunflower embryos by 5 days post-fertilization (DPF), 2 days before helianthinins are detectable, and continue to accumulate through seed maturation. Sunflower albumin mRNAs, also first detected at 5 DPF, accumulate rapidly in sunflower embryos reaching maximum prevalence between 12 and 15 DPF. After this time albumin transcripts decrease in prevalence with kinetics similar to that observed for helianthinin mRNA (Allen et al. 1987). Functional sunflower albumin mRNAs are undetectable in dry seeds, germinated seedlings or leaves (Cohen 1986).

A number of albumin cDNAs and genomic clones have been isolated from different plant species including sunflower (Allen et al. 1987 *Mol-Gen Genet.* 210:211–218) and pea (Higgins et al. 1986 *J. Biol. Chem* 261:11124–11130). As in other classes of seed proteins such as *Brassica napis* (Crouch et al., 1983; Ericson et al., 1986), 2S albumin seed proteins are encoded by small gene families.

The present invention provides 5' regulatory sequences from a sunflower albumin gene which direct high level expression of lipid metabolism genes in transgenic plants. In accordance with the present invention, chimeric constructs comprising a sunflower albumin 5' regulatory region operably linked to coding sequence for a lipid metabolism gene such as a Δ6-desaturase gene are provided. Transgenic plants comprising the subject chimeric constructs accumulate GLA to approximately 10% of C18 fatty acids. This is within the range of accumulation of GLA for *Oenothera biennis*, a primary commercial source for GLA.

SUMMARY OF THE INVENTION

The present invention is directed to 5' regulatory regions of a sunflower albumin gene. The 5' regulatory regions, when operably linked to either the coding sequence of a heterologous gene or sequence complementary to a native plant gene, direct expression of the heterologous gene or complementary sequence in a plant seed.

The present invention thus provides expression cassettes and expression vectors comprising an albumin 5' regulatory region operably linked to a heterologous gene or a sequence complementary to a native plant gene.

Plant transformation vectors comprising the expression cassettes and expression vectors are also provided as are plant cells transformed by these vectors, and plants and their progeny containing the vectors.

In one embodiment of the invention, the heterologous gene or complementary sequence is a fatty acid synthesis gene or a lipid metabolism gene.

In another aspect of the present invention, a method is provided for producing a plant with increased levels of a product of a fatty acid synthesis or lipid metabolism gene.

In particular, there is provided a method for producing a plant with increased levels of a fatty acid synthesis or lipid metabolism gene by transforming a plant with the subject expression cassettes and expression vectors which comprise an albumin 5' regulatory region and a coding sequence for a fatty acid synthesis or lipid metabolism gene.

In another aspect of the present invention, there is provided a method for cosuppressing a native fatty acid synthesis or lipid metabolism gene by transforming a plant with the subject expression cassettes and expression vectors which comprise an albumin 5' regulatory region and a coding sequence for a fatty acid synthesis or lipid metabolism gene.

A further aspect of this invention provides a method of decreasing production of a native plant gene such as a fatty acid synthesis gene or a lipid metabolism gene by transforming a plant with an expression vector comprising an albumin 5' regulatory region operably linked to a nucleic acid sequence complementary to a native plant gene.

Also provided are methods of modulating the levels of a heterologous gene or native plant gene such as a fatty acid synthesis or lipid metabolism gene by transforming a plant with the subject expression cassettes and expression vectors.

BRIEF DESCRIPTION OF THE DRAWINGS

FIG. 1 depicts the nucleotide and corresponding amino acid sequence of the borage Δ6-desaturase gene (SEQ ID NO:1). The cytochrome b5 heme-binding motif is boxed and the putative metal binding, histidine rich motifs (HRMs) are underlined.

FIG. 4 is the nucleotide sequence of the HaG5 regulatory region. The transcriptional start site (+1) is indicated by a bold T. The underlined Bam HI restriction site was introduced by PCR.

DETAILED DESCRIPTION OF THE INVENTION

Figure 2:
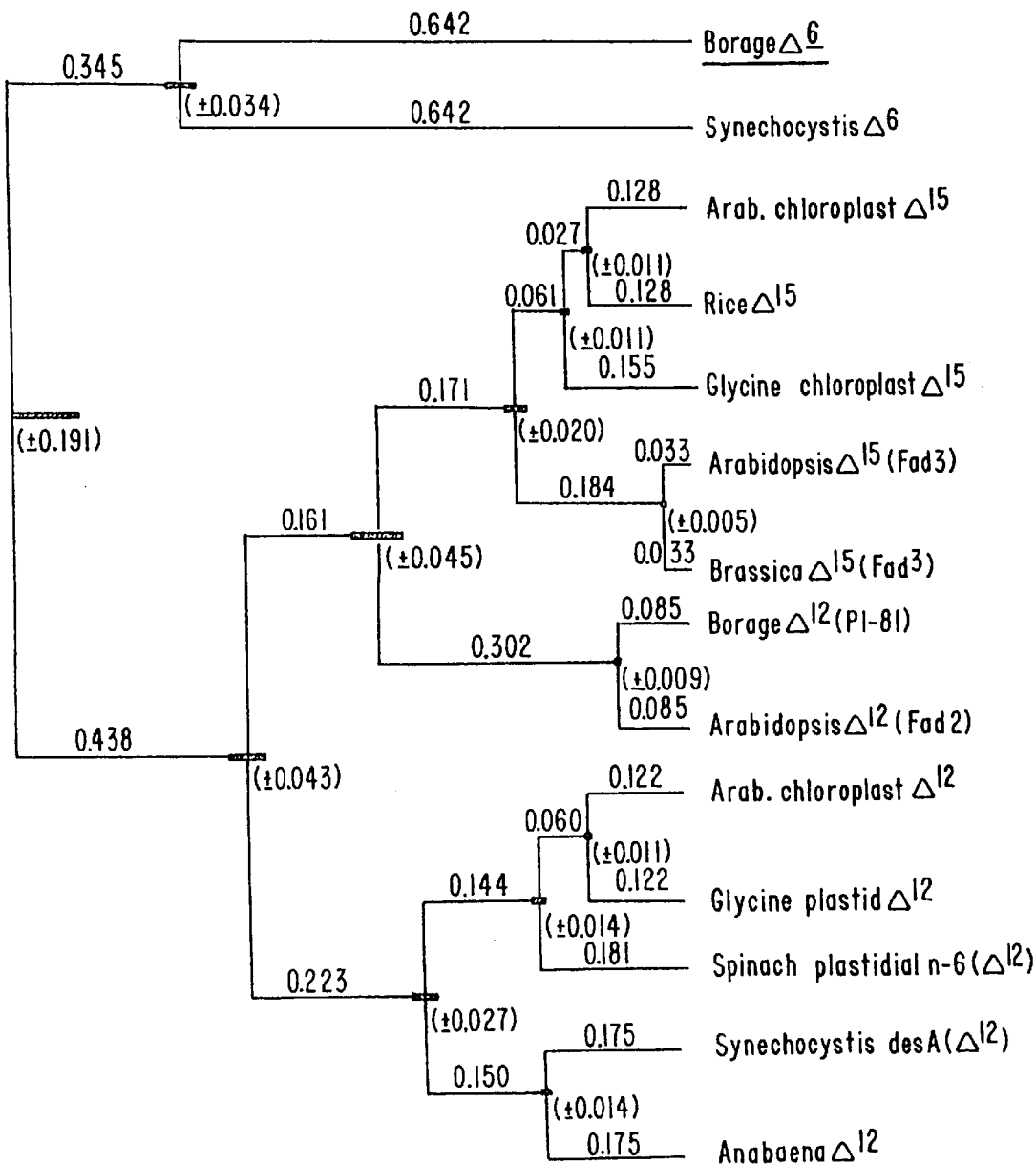
FIG. 2 is a dendrogram showing similarity of the borage Δ6-desaturase to other membrane-bound desaturases. The amino acid sequence of the borage Δ6-desaturase was compared to other known desaturases using Gene Works (IntelliGenetics). Numerical values correlate to relative phylogenetic distances between subgroups compared.

The present invention provides isolated nucleic acids encoding 5' regulatory regions from a sunflower albumin gene. In accordance with the present invention, the subject 5' regulatory regions, when operably linked to either a coding sequence of a heterologous gene or sequence complementary to a native plant gene, direct expression of the coding sequence or the complementary sequence in a plant seed. The albumin 5' regulatory regions of the present invention are useful in the construction of an expression cassette which comprises in the 5' to 3' direction, a subject albumin 5' regulatory region, a heterologous gene or sequence complementary to a native plant gene under control of the regulatory region and a 3' termination sequence. Such an expression cassette can be incorporated into a variety of autonomously replicating vectors in order to construct an expression vector.

In accordance with the present invention, it has been surprisingly found that plants transformed with a subject expression vector accumulate GLA to approximately 10% of C18 fatty acids. Such an accumulation is within the range of accumulation of GLA for *Oenothera biennis*, a primary commercial source for GLA.

As used herein, the term "cassette" refers to a nucleotide sequence capable of expressing a particular gene if said gene is inserted so as to be operably linked to one or more regulatory regions present in the nucleotide sequence. Thus, for example, the expression cassette may comprise a heterologous coding sequence which is desired to be expressed in a plant seed. The expression cassettes and expression vectors of the present invention are therefore useful for directing seed-specific expression of any number of heterologous genes. The term "seed-specific expression" as used herein, refers to expression in various portions of a plant seed such as the endosperm and embryo.

An isolated nucleic acid encoding a 5' regulatory region from a sunflower albumin gene can be provided as follows. Albumin recombinant genomic clones are isolated by screening a sunflower genomic DNA library with a cDNA (or a portion thereof) representing albumin mRNA. A number of different albumin cDNAs have been isolated. The methods used to isolate such cDNAs as well as the nucleotide and corresponding amino acid sequences have been published. Higgins et al., 1986 *J. Biol. Chem.* 261: 11124–11130; Allen et al., 1987 in Molecular Approaches to Developmental Biology, Alan R. Liss, Inc., pp. 415–424.

Methods considered useful in obtaining albumin genomic recombinant DNA are provided in Sambrook et al. 1989, in *Molecular Cloning: A Laboratory Manual*, Cold Spring Harbor, N.Y., for example, or any of the myriad of laboratory manuals on recombinant DNA technology that are widely available. To determine nucleotide sequences, a multitude of techniques are available and known to the ordinarily skilled artisan. For example, restriction fragments containing an albumin regulatory region can be subcloned into the polylinker site of a sequencing vector such as pBluescript (Stratagene). These pBluescript subclones can then be sequenced by the double-stranded dideoxy method (Chen and Seeburg, 1985, *DNA* 4:165).

In a preferred embodiment, the sunflower albumin regulatory region comprises nucleotides 858 to +29 of FIG. 4 (nucleotides 1–895 of SEQ ID NO:2). Modifications to the albumin regulatory region as set forth in SEQ ID NO:2 which maintain the characteristic property of directing seed-specific expression, are within the scope of the present invention. Such modifications include insertions, deletions and substitutions of one or more nucleotides.

The 5' regulatory region of the present invention can be derived from restriction endonuclease or exonuclease digestion of an albumin genomic clone. Thus, for example, the known nucleotide or amino acid sequence of the coding region of an isolated albumin gene is aligned to the nucleic acid or deduced amino acid sequence of an isolated albumin genomic clone and 5' flanking sequence (i.e., sequence upstream from the translational start codon of the coding region) of the isolated albumin genomic clone located.

The albumin 5' regulatory region as set forth in SEQ ID NO:2 (nucleotides –860 to +29 of FIG. 9) may be generated from a genomic clone having either or both excess 5' flanking sequence or coding sequence by exonuclease III-mediated deletion. This is accomplished by digesting appropriately prepared DNA with exonuclease III (exoIII) and removing aliquots at increasing intervals of time during the digestion. The resulting successively smaller fragments of DNA may be sequenced to determine the exact endpoint of the deletions. There are several commercially available systems which use exonuclease III (exoIII) to create such a deletion series, e.g. Promega Biotech, "Erase-A-Base" system. Alternatively, PCR primers can be defined to allow direct amplification of the subject 5' regulatory regions.

Using the same methodologies, the ordinarily skilled artisan can generate one or more deletion fragments of nucleotides 1–895 as set forth in SEQ ID NO:2. Any and all deletion fragments which comprise a contiguous portion of nucleotides set forth in SEQ ID NO:2 and which retain the capacity to direct seed-specific expression are contemplated by the present invention.

The identification of albumin 5' regulatory sequences which direct seed-specific expression comprising nucleotides 1–895 of SEQ ID NO:2 and modifications or deletion fragments thereof, can be accomplished by transcriptional fusions of specific sequences with the coding sequences of a heterologous gene, transfer of the chimeric gene into an appropriate host, and detection of the expression of the heterologous gene. The assay used to detect expression depends upon the nature of the heterologous sequence. For example, reporter genes, exemplified by chloramphenicol acetyl transferase and β-glucuronidase (GUS), are commonly used to assess transcriptional and translational competence of chimeric constructions. Standard assays are available to sensitively detect the reporter enzyme in a transgenic organism. The β-glucuronidase (GUS) gene is useful as a reporter of promoter activity in transgenic plants because of the high stability of the enzyme in plant cells, the lack of intrinsic β-glucuronidase activity in higher plants and availability of a quantitative fluorimetric assay and a histochemical localization technique. Jefferson et al. (1987 *EMBO J* 6:3901) have established standard procedures for biochemical and histochemical detection of GUS activity in plant tissues. Biochemical assays are performed by mixing plant tissue lysates with 4-methylumbelliferyl-β-D-glucuronide, a fluorimetric substrate for GUS, incubating one hour at 37° C., and then measuring the fluorescence of the resulting 4-methyl-umbelliferone. Histochemical localization for GUS activity is determined by incubating plant tissue samples in 5-bromo-4-chloro-3-indolyl-glucuronide (X-Gluc) for about 18 hours at 37° C. and observing the staining pattern of X-Gluc. The construction of such chimeric genes allows definition of specific regulatory sequences and demonstrates that these sequences can direct expression of heterologous genes in a seed-specific manner.

Another aspect of the invention is directed to a chimeric plant gene comprising a 5' regulatory region from an albumin gene which directs seed specific expression operably linked to the coding sequence of a heterologous gene such that the regulatory element is capable of controlling expression of the product encoded by the heterologous gene. The heterologous gene can be any gene other than albumin. If necessary, additional regulatory elements or parts of these elements sufficient to cause expression resulting in production of an effective amount of the polypeptide encoded by the heterologous gene are included in the chimeric constructs.

Accordingly, the present invention provides chimeric genes comprising sequences of the albumin 5' regulatory region that confer seed-specific expression which are operably linked to a sequence encoding a heterologous gene such as a lipid metabolism enzyme. Examples of lipid metabolism and fatty acid synthesis genes useful for practicing the present invention include lipid desaturases such as Δ6-desaturases, Δ12-desaturases, Δ15-desaturases and other related desaturases such as stearoyl-ACP desaturases, acyl carrier proteins (ACPs), thioesterases, acetyl transacylases, acetyl-coA carboxylases, ketoacyl-synthases, malonyl transacylases, and elongases. Such lipid metabolism and fatty acid synthesis genes have been isolated and characterized from a number of different bacteria and plant species. Their nucleotide coding sequences as well as methods of isolating such coding sequences are disclosed in the published literature and are widely available to those of skill in the art.

In particular, the Δ6-desaturase genes disclosed in U.S. Pat. No. 5,552,306 and applicants' copending U.S. application Ser. No. 08/366,779 filed Dec. 30, 1994 and incorporated herein by reference, are contemplated as lipid metabolism genes particularly useful in the practice of the present invention.

The chimeric genes of the present invention are constructed by ligating a 5' regulatory region of an albumin genomic DNA to the coding sequence of a heterologous gene. The juxtaposition of these sequences can be accomplished in a variety of ways. In a preferred embodiment the order of the sequences, from 5' to 3', is an albumin 5' regulatory region (including a promoter), a coding sequence, and a termination sequence which includes a polyadenylation site.

Standard techniques for construction of such chimeric genes are well known to those of ordinary skill in the art and can be found in references such as Sambrook et al. (1989). A variety of strategies are available for ligating fragments of DNA, the choice of which depends on the nature of the termini of the DNA fragments. One of ordinary skill in the art recognizes that in order for the heterologous gene to be expressed, the construction requires promoter elements and signals for efficient polyadenylation of the transcript. Accordingly, the albumin 5' regulatory region that contains the consensus promoter sequence known as the TATA box can be ligated directly to a promoterless heterologous coding sequence.

The restriction or deletion fragments that contain the albumin TATA box are ligated in a forward orientation to a promoterless heterologous gene such as the coding sequence of β-glucuronidase (GUS). The skilled artisan will recognize that the subject albumin 5' regulatory regions can be provided by other means, for example chemical or enzymatic synthesis. The 3' end of a heterologous coding sequence is optionally ligated to a termination sequence comprising a polyadenylation site, exemplified by, but not limited to, the nopaline synthase polyadenylation site, or the octopine T-DNA gene 7 polyadenylation site. Alternatively, the polyadenylation site can be provided by the heterologous gene.

The present invention also provides methods of increasing levels of heterologous genes in plant seeds. In accordance with such methods, the subject expression cassettes and expression vectors are introduced into a plant in order to effect expression of a heterologous gene. For example, a method of producing a plant with increased levels of a product of a fatty acid synthase or lipid metabolism gene is provided by transforming a plant cell with an expression vector comprising an albumin 5' regulatory region operably linked to a fatty acid synthesis or lipid metabolism gene and regenerating a plant with increased levels of the product of said fatty acid synthesis or lipid metabolism gene.

Another aspect of the present invention provides methods of reducing levels of a product of a gene which is native to a plant which comprises transforming a plant cell with an expression vector comprising a subject albumin regulatory region operably linked to a nucleic acid sequence which is complementary to the native plant gene. In this manner, levels of endogenous product of the native plant gene are reduced through the mechanism known as antisense regulation. Thus, for example, levels of a product of a fatty acid synthesis gene or lipid metabolism gene are reduced by transforming a plant with an expression vector comprising a subject albumin 5' regulatory region operably linked to a nucleic acid sequence which is complementary to a nucleic acid sequence coding for a fatty acid synthesis or lipid metabolism gene.

The present invention also provides a method of cosuppressing a gene which is native to a plant which comprises transforming a plant cell with an expression vector comprising a subject albumin regulatory region operably linked to a nucleic acid sequence coding for the native plant gene. In this manner, levels of endogenous product of the native plant gene are reduced through the mechanism known as cosuppression. Thus, for example, levels of a product of a fatty acid synthesis gene or lipid metabolism gene are reduced by transforming a plant with an expression vector comprising a subject albumin 5' regulatory region operably linked to a nucleic acid sequence coding for a fatty acid synthesis or lipid metabolism gene native to the plant. Although the exact mechanism of cosuppression is not completely undertood, one skilled in the art is familiar with published works reporting the experimental conditions and results associated with cosuppression (Napoli et al. 1990 *The Plant Cell* 2:270–289; Van der Krol 1990 *The Plant Cell* 2:291–299.

To provide regulated expression of the heterologous or native genes, plants are transformed with the chimeric gene constructions of the invention. Methods of gene transfer are well known in the art. The chimeric genes can be introduced into plants by leaf disk transformation-regeneration procedure as described by Horsch et al. (1985) *Science* 227:1229. Other methods of transformation such as protoplast culture (Horsch et al. 1984 *Science* 223:496, DeBlock et al. 1984 *EMBO J*. 2:2143, Barton et al. 1983, *Cell* 32:1033) can also be used and are within the scope of this invention. In a preferred embodiment, plants are transformed with Agrobacterium-derived vectors such as those described in Klett et al. (1987) *Annu. Rev. Plant Physiol.* 38:467. Other well-known methods are available to insert the chimeric genes of the present invention into plant cells. Such alternative methods include biolistic approaches (Klein et al. 1987 *Nature* 327:70), electroporation, chemically-induced DNA uptake, and use of viruses or pollen as vectors.

When necessary for the transformation method, the chimeric genes of the present invention can be inserted into a plant transformation vector, e.g. the binary vector described by Bevan, M. 1984 *Nucl. Acids Res.* 12:8711–8721. Plant transformation vectors can be derived by modifying the natural gene transfer system of *Agrobacterium tumefaciens*. The natural system comprises large Ti (tumor-inducing)-plasmids containing a large segment, known as T-DNA, which is transferred to transformed plants. Another segment of the Ti plasmid, the vir region, is responsible for T-DNA transfer. The T-DNA region is bordered by terminal repeats. In the modified binary vectors, the tumor inducing genes have been deleted and the functions of the vir region are utilized to transfer foreign DNA bordered by the T-DNA border sequences. The T-region also contains a selectable marker for antibiotic resistance, and a multiple cloning site for inserting sequences for transfer. Such engineered strains are known as "disarmed" *A. tumefaciens* strains, and allow the efficient transfer of sequences bordered by the T-region into the nuclear genome of plants.

Surface-sterilized leaf disks or other susceptable tissues are inoculated with the "disarmed" foreign DNA-containing *A. tumefaciens*, cultured for a number of days, and then transferred to antibiotic-containing medium. Transformed shoots are then selected after rooting in medium containing the appropriate antibiotic, and transferred to soil. Transgenic plants are pollinated and seeds from these plants are collected and grown on antibiotic medium.

Expression of a heterologous or reporter gene in developing seeds, young seedlings and mature plants can be monitored by immunological, histochemical or activity assays. As discussed herein, the choice of an assay for expression of the chimeric gene depends upon the nature of the heterologous coding region. For example, Northern analysis can he used to assess transcription if appropriate nucleotide probes are available. If antibodies to the polypeptide encoded by the heterologous gene are available, Western analysis and immunohistochemical localization can be used to assess the production and localization of the polypeptide. Depending upon the heterologous gene, appropriate biochemical assays can be used. For example, acetyltransferases are detected by measuring acetylation of a standard substrate. The expression of a lipid desaturase gene can be assayed by analysis of fatty acid methyl esters (FAMES).

Another aspect of the present invention provides transgenic plants or progeny of these plants containing the chimeric genes of the invention. Both monocotyledonous and dicotyledonous plants are contemplated. Plant cells are transformed with the chimeric genes by any of the plant transformation methods described above. The transformed plant cell, usually in the form of a callus culture, leaf disk or whole plant (via the vacuum infiltration method of Bechtold et al. 1993 *C.R. Acad. Sci. Paris*, 316:1194–1199) is regenerated into a complete transgenic plant by methods well-known to one of ordinary skill in the art (e.g. Horsh et al. 1985 *Science* 227:1129). In a preferred embodiment, the transgenic plant is sunflower, cotton, oil seed rape, maize, tobacco, Arabidopsis, peanut or soybean. Since progeny of transformed plants inherit the chimeric genes, seeds or cuttings from transformed plants are used to maintain the transgenic line.

The following examples further illustrate the invention.

EXAMPLE 1

Isolation of Membrane-Bound Polysomal RNA and Construction of Borage cDNA Library Membrane-bound polysomes were isolated from borage seeds 12 days post pollination (12 DPP) using the protocol established for peas by Larkins and Davies (1975 *Plant Phys.* 55: 749–756). RNA was extracted from the polysomes as described by Mechler (1987 *Methods in Enzymology* 152: 241–248, Academic Press). Poly-A$^+$ RNA was isolated from the membrane bound polysomal RNA using Oligotex-dT™ beads (Qiagen).

Corresponding cDNA was made using Stratagene's ZAP cDNA synthesis kit. The cDNA library was constructed in the lambda ZAP II vector (Stratagene) using the lambda ZAP II kit. The primary library was packaged with Gigapack II Gold packaging extract (Stratagene).

EXAMPLE 2

Isolation of a Δ-6 Desaturase cDNA from Borage
Hybridization protocol

The amplified borage cDNA library was plated at low density (500 pfu on 150 mm petri dishes). Highly prevalent seed storage protein cDNAs were reduced (subtracted from the total cDNAs) by screening with the corresponding cDNAs.

Hybridization probes for screening the borage cDNA library were generated by using random primed DNA synthesis as described by Ausubel et al (1994 *Current Protocols in Molecular Biology*, Wiley Interscience, N.Y.) and corresponded to previously identified abundantly expressed seed storage protein cDNAs. Unincorporated nucleotides were removed by use of a G-50 spin column (Boehringer Manheim). Probe was denatured for hybridization by boiling in a water bath for 5 minutes, then quickly cooled on ice. Nitrocellulose filters carrying fixed recombinant bacteriophage were prehybridized at 60° C. for 2–4 hours in hybridization solution [4× SET (600 mM NaCl, 80 mM Tris-HCl, 4 mM Na$_2$EDTA; pH 7.8), 5× Denhardt's reagent (0.1% bovine serum albumin, 0.1% Ficoll, and 0.1% polyvinylpyrolidone), 100 µg/ml denatured salmon sperm DNA, 50 µg/ml polyadenine and 10 ug/ml polycytidine]. This was replaced with fresh hybridization solution to which denatured radioactive probe (2 ng/ml hybridization solution) was added. The filters were incubated at 60° C. with agitation overnight. Filters were washed sequentially in 4×, 2×, and 1× SET (150 mM NaCl, 20 mM Tris-HCl, 1 mM Na$_2$EDTA; pH7.8) for 15 minutes each at 60° C. Filters were air dried and then exposed to X-ray film for 24 hours with intensifying screens at −80° C.

Non-hybridizing plaques were excised using Stratagene's excision protocol and reagents. Resulting bacterial colonies were used to inoculate liquid cultures and were either sequenced manually or by an ABI automated sequencer.
Random Sequencing of cDNAs from a Borage Seed 12 (DPP) Membrane-Bound Polysomal Library Each cDNA corresponding to a non-hybridizing plaque was sequenced once and a sequence tag generated from 200–300 base pairs. All sequencing was performed by cycle sequencing (Epicentre). Over 300 expressed sequence tags (ESTs) were generated. Each sequence tag was compared to GenBank database using the BLAST algorithm (Altschul et al. 1990 *J. Mol. Biol.* 215:403–410). A number of lipid metabolism genes, including the Δ6-desaturase were identified.

Database searches with the cDNA clone designated mbp-65 using BLASTX with the GenBank database resulted in a significant match to the previously isolated Synechocystis Δ6-desaturase. It was determined however, that mbp-65 was not a full length cDNA. A full length cDNA was isolated using mbp-65 to screen the borage membrane-bound polysomal library. The resultant clone was designated pAN1 and the cDNA insert of pAN1 was sequenced by the cycle sequencing method. The amino acid sequence deduced from the open reading frame (FIG. 1, SEQ ID NO:1) was compared to other known desaturases using Geneworks (IntelligGenetics) protein alignment program. This alignment indicated that the cDNA insert of pAN1 was the borage Δ6-desaturase gene.

The resulting dendrogram (FIG. 2) shows that $\Delta^{15}$-desaturases and $\Delta^{12}$-desaturases comprise two groups. The newly isolated borage sequence and the previously isolated Synechocystis Δ$^6$-desaturase (U.S. Pat. No. 5,552,306) formed a third distinct group. A comparison of amino acid motifs common to desaturases and thought to be involved catalytically in metal binding illustrates the overall similarity of the protein encoded by the borage gene to desaturases in general and the Synechocystis Δ$^6$-desaturase in particular (Table 1). At the same time, comparison of the motifs in Table 1 indicates definite differences between this protein and other plant desaturases. Furthermore, the borage sequence is also distinguished from known plant membrane associated fatty acid desaturases by the presence of a heme binding motif conserved in cytochrome b$_5$ proteins (Schmidt et al. 1994 *Plant Mol. Biol.* 26:631–642) (FIG. 1). Thus, while these results clearly suggested that the isolated cDNA was a borage Δ$^6$-desaturase gene, further confirmation was necessary. To confirm the identity of the borage Δ6-desaturase cDNA, the cDNA insert from pAN1 was cloned into an expression cassette for stable expression. The vector pBI121 (Jefferson et al. 1987 EMBO J. 6:3901–3907)

was prepared for ligation by digestion with BamHI and EcoICR I (an isoschizomer of SacI which leaves blunt ends; available from Promega) which excises the GUS coding region leaving the 35S promoter and NOS terminator intact. The borage $\Delta^6$-desaturase cDNA was excised from the recombinant plasmid (pAN1) by digestion with BamHI and XhoI. The XhoI end was made blunt by performing a fill-in reaction catalyzed by the Klenow fragment of DNA polymerase I. This fragment was then cloned into the BamHI/EcoICR I sites of pBI121.1, resulting in the plasmid pAN2.

EXAMPLE 3

Production of Transgenic Plants and Preparation and Analysis of Fatty Acid Methyl Esters (FAMEs)

The expression plasmid, pAN2 was used to transform tobacco (*Nicotiana tabacum* cv. *xanthi*) via *Agrobacteritum tumefaciens* according to standard procedures (Horsch, et al. 1985 *Science* 227:1229–1231; Bogue et al. 1990 *Mol. Gen. Genet.* 221:49–57) except that the initial transformants were selected on 100 µg/ml kanamycin.

Tissue from transgenic plants was frozen in liquid nitrogen and lyophilized overnight. FAMEs were prepared as described by Dahmer, et al. (1989) *J. Amer. Oil. Chem. Soc.* 66: 543–548. In some cases, the solvent was evaporated again, and the FAMEs were resuspended in ethyl acetate and extracted once with deionized water to remove any water soluble contaminants. FAMEs were analyzed using a Tracor-560 gas liquid chromatograph as previously described (Reddy et al. 1996 *Nature Biotech.* 14:639–642).

Figures 3A, 3B:
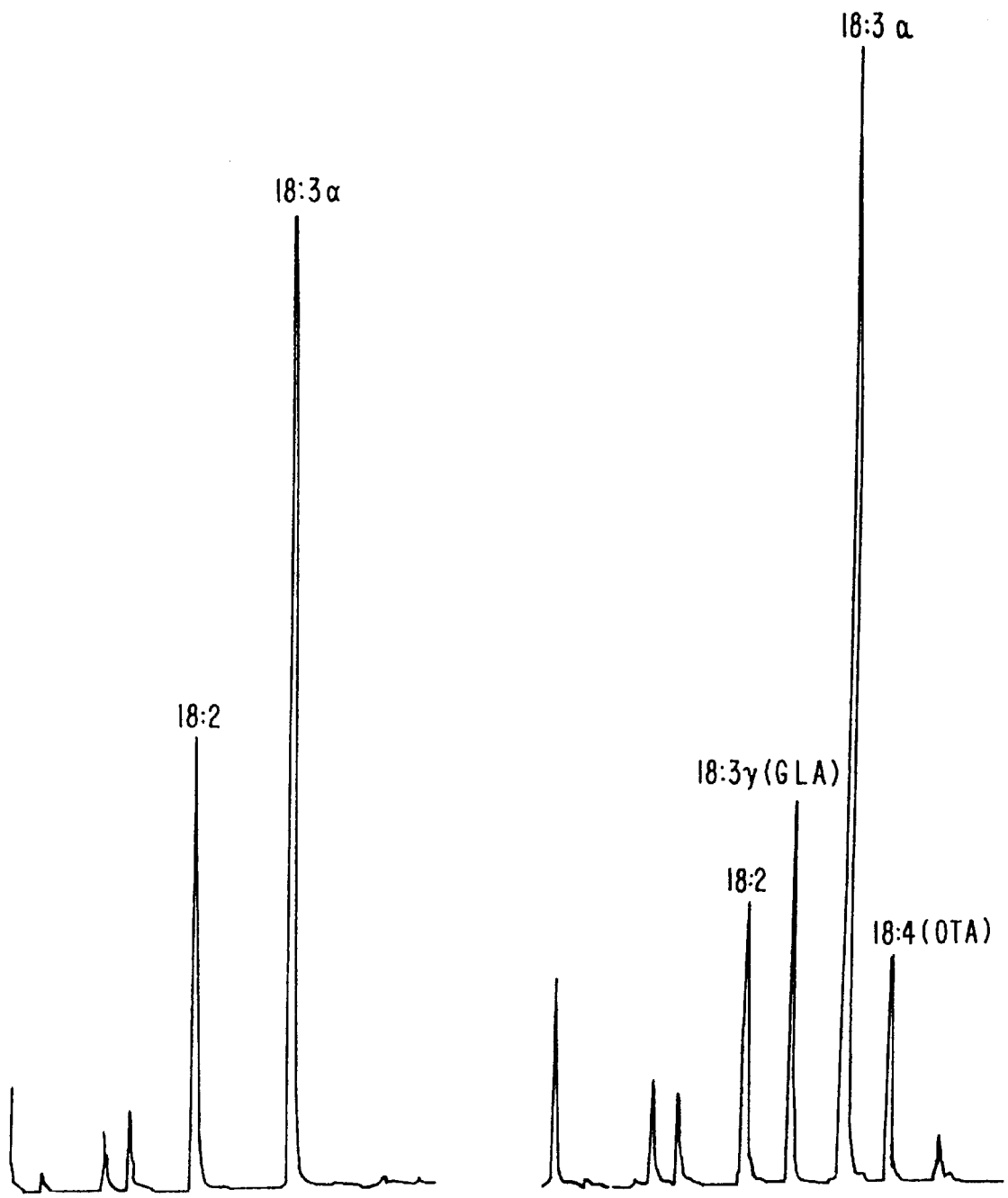
FIG. 3A provides a gas liquid chromatography profile of the fatty acid methyl esters (FAMES) derived from leaf tissue of a wild type tobacco 'Xanthi'.
FIG. 3B provides a gas liquid chromatography profile of the FAMES derived from leaf tissue of a tobacco plant transformed with the borage Δ6-desaturase cDNA under transcriptional control of the CaMV 35S promoter (pAN2). Peaks corresponding to methyl linoleate (18:2), methyl γ-linolenate (18:3γ), methyl α-linolenate (18:3α), and methyl octadecatetraenoate (18:4) are indicated.

As shown in FIG. 3, transgenic tobacco leaves containing the borage cDNA produced both GLA and octadecatetraenoic acid (OTA) (18:4 $\Delta$6,9,12,15). These results thus demonstrate that the isolated cDNA encodes a borage $\Delta$6-desaturase.

EXAMPLE 4

Expression of $\Delta$6-desaturase in Borage

The native expression of $\Delta$6-desaturase was examined by Northern Analysis of RNA derived from borage tissues. RNA was isolated from developing borage embryos following the method of Chang et al. 1993 *Plant Mol. Biol. Rep.* 11:113–116. RNA was electrophoretically separated on formaldehyde-agarose gels, blotted to nylon membranes by capillary transfer, and immobilized by baking at 80° C. for 30 minutes following standard protocols (Brown T., 1996 in *Current Protocols in Molecular Biology*, eds. Auselbel, et al. [Greene Publishing and Wiley-Interscience, New York] pp. 4.9.1–4.9.14.). The filters were preincubated at 42° C. in a solution containing 50% deionized formamide, 5× Denhardt's reagent, 5× SSPE (900 mM NaCl; 50 mM Sodium phosphate, pH7.7; and 5 mM EDTA), 0.1% SDS, and 200 µ/g/ml denatured salmon sperm DNA. After two hours, the filters were added to a fresh solution of the same composition with the addition of denatured radioactive hybridization probe. In this instance, the probes used were borage legumin cDNA (FIG. 16A), borage oleosin cDNA (FIG. 16B), and borage $\Delta$6-desaturase cDNA (pAN1, Example 2) (FIG. 16C). The borage legumin and oleosin cDNAs were isolated by EST cloning and identified by comparison to the GenBank database using the BLAST algorithm as described in Example 2. Loading variation was corrected by normalizing to levels of borage EF1α mRNA. EF1α mRNA was identified by correlating to the corresponding cDNA obtained by the EST analysis described in Example 2. The filters were hybridized at 42° C. for 12–20 hours, then washed as described above (except that the temperature was 65° C.), air dried, and exposed to X-ray film.

As depicted in FIGS. 15A and 15B, $\Delta$6-desaturase is expressed primarily in borage seed. Borage seeds reach maturation between 18–20 days post pollination (dpp). $\Delta$6-desaturase mRNA expression occurs throughout the time points collected (8–20 dpp), but appears maximal from 10–16 days post pollination. This expression profile is similar to that seen for borage oleosin and 12S seed storage protein mRNAs (FIGS. 16A, 16B, and 16C).

EXAMPLE 5

ISOLATION OF A SUNFLOWER ALBUMIN cDNA

The sunflower albumin cDNA (Ha5) was isolated by differentially screening a sunflower cDNA library using cDNA probes from leaf and 12 DPF (days post flowering) embryos. A cDNA of 1011 bp was obtained (Cohen E. A. "Analysis of sunflower 2S seed storage protein genes" MS thesis, Texas A&M University, Allen et al., 1987a in *Molecular Approaches to Developmental Biology*, pp. 415–424.). Although not full length, the cDNA comprised most of the coding sequence for the sunflower 2S albumin. Northern and dot blot analysis indicated that this gene is exclusively expressed in developing sunflower seeds. Albumin transcripts and protein are first detected 5 DPF, a full two days earlier than helianthinin (11S), and reach maximal prevalence around 12–15 DPF (Allen et al. 1987a).

EXAMPLE 6

ISOLATION OF A SUNFLOWER ALBUMIN 5' REGULATORY REGION

Genomic clones were isolated by screening a sunflower genomic DNA library using the Ha5 cDNA as a probe. Four independent genomic clones were shown to be identical by restriction enzyme digestion. Therefore, one clone (HaG5) was chosen for more detailed analysis.

A 2.3 kb EcoRI/DraI fragment was sequenced (Allen et al., 1987b *Mol. Gen. Genet.* 210: 211–218). The HaG5 albumin gene contains two exons. The first exon (exon 1) is 575 nucleotides in length and the second exon (exon 2) is 310 nucleotides in length. A 190 nucleotide intron separates the two exons. Nuclease protection experiments showed that the transcription start site was located 30 nucleotides upstream of the translational start site. (Allen et al 1987b, FIG. 2). Southern analysis of genomic DNA and the fact that only one gene was isolated in an exhaustive screen indicated that HaG5 is a single copy gene in the sunflower genome.

Figure 5:
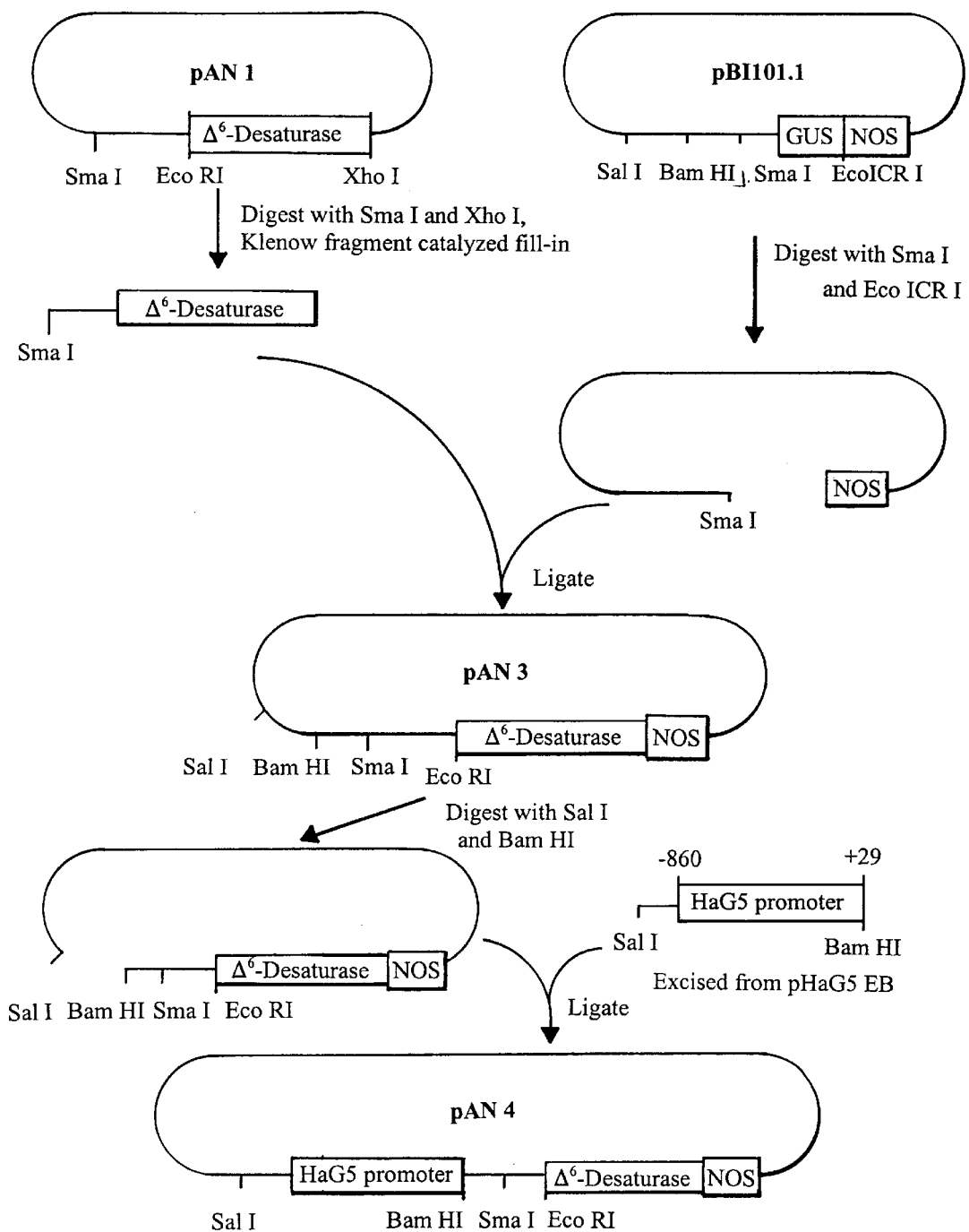
FIG. 5 is a scheme depicting construction of the sunflower albumin HaG5 regulatory region/Δ6-desaturase gene expression vector.
Figure 6A:
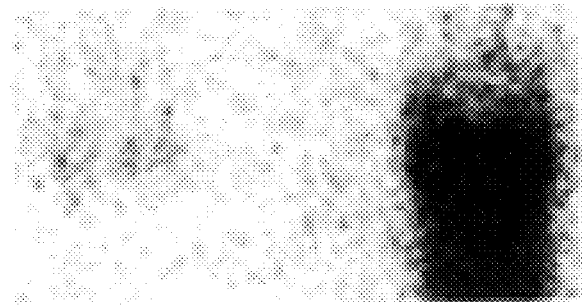
FIG. 6A is an RNA gel blot analysis carried out on 5 μg samples of RNA isolated from borage leaf, root, and 12 dpp embryo tissue, using labeled borage Δ6-desaturase cDNA as a hybridization probe.
Figure 6B:
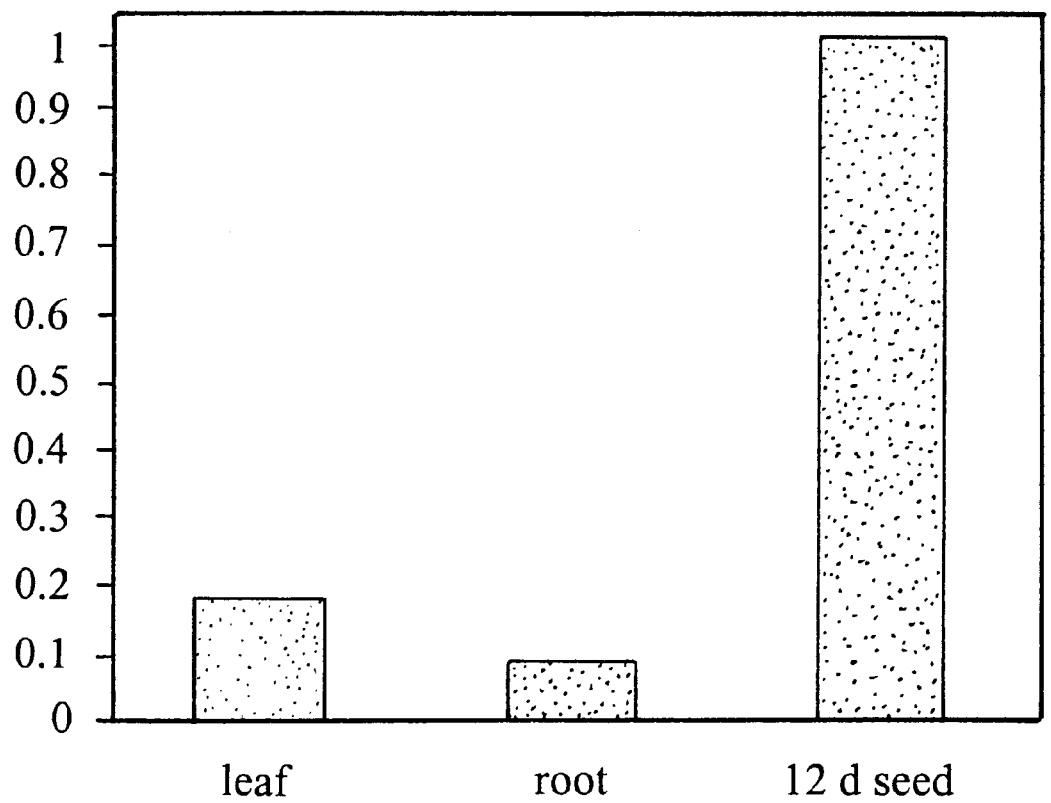
FIG. 6B depicts a graph corresponding to the Northern analysis results for the experiment shown in FIG. 6A.

An 889 bp upstream regulatory region (−860 to +29 of FIG. 4; SEQ ID NO:2) was cloned in several steps from HaG5. A 1.1 kb EcoRI fragment was subcloned in PBluescript™ (Stratagene) yielding pHaG5RI. PCR was performed on pHaG5RI with primers that resulted in the albumin 5' regulatory region being flanked by EcoRI and BamHI sites at the 5' and 3' ends, respectively. The restriction fragment was cloned into the EcoRI/BamHI sites of pBluescript™ yielding pHaG5EB. Individual clones were sequenced to check possible PCR mutations as well as the orientation of their inserts. The sequence of the albumin 5' regulatory region is shown in FIG. 4 (SEQ. ID NO:2). The SalI/BamHI fragment of this construct was excised and cloned into pAN3 (the parental borage $\Delta$6-desaturase containing plasmid), yielding pAN4. A map of pAN4 and the intermediate vectors involved in its construction are shown in FIG. 5. pAN1 is described in Example 2. pBI101.1 is described in (Jefferson et al. 1987 *EMBO J.* 6:3901–3907).

EXAMPLE 7

EXPRESSION OF Δ6-DESATURASE UNDER CONTROL OF THE SUNFLOWER ALBUMIN 5' REGULATORY REGION

The albumin 5' regulatory region was used to drive the expression of a borage Δ6-desaturase gene in Arabidopis. pAN4 was used to transform Arabidopsis using the vacumme inflitration method of Bechtold et al. 1993 *C.R. Acad. Sci. Paris* 316: 1194–1199. Levels of Δ6-desaturase activity were monitored by assaying the corresponding fatty acid methyl esters of its reaction products, γ-linolenic acid (GLA) and octadecatetraenoic acid (OTA) using the methods described in Example 3. GLA and OTA levels in transgenic seeds ranged up to 10.2% (average of 4.4%) and 3.6% (average of 1.7%), respectively, of the C18 fatty acids. No GLA or OTA was detected in the leaves of these plants. In comparison, 35S promoter/$\Delta^6$-desaturase transgenic plants produced GLA levels of up to 3.1% of C18 fatty acids (average of 1.3%) in leaves and no measurable OTA in seeds. These data are summarized in Table 2.

TABLE 1

COMPARISON OF COMMON AMINO ACID MOTIFS IN MEMBRANE-BOUND DESATURASES

| Desaturase | Lipid Box | | Metal Box 1 | | Metal Box 2 | |
|---|---|---|---|---|---|---|
| Borage $\Delta^6$ | WIGHDAGH | (SEQ. ID. NO: 3) | HNAHH | (SEQ. ID. NO: 9) | FQIEHH | (SEQ. ID. NO: 17) |
| Synechocystis $\Delta^6$ | NVGHDANH | (SEQ. ID. NO: 4) | HNYLHH | (SEQ. ID. NO: 10) | HQVTHH | (SEQ. ID. NO: 18) |
| Arab. chloroplast $\Delta^{15}$ | VLGHDCGH | (SEQ. ID. NO: 5) | HRTHH | (SEQ. ID. NO: 11) | HVIHH | (SEQ. ID. NO: 19) |
| Rice $\Delta^{15}$ | VLGHDCGH | (SEQ. ID. NO: 5) | HRTHH | (SEQ. ID. NO: 11) | HVIHH | (SEQ. ID. NO: 19) |
| Glycine chloroplast $\Delta^{15}$ | VLGHDCGH | (SEQ. ID. NO: 5) | HRTHH | (SEQ. ID. NO: 11) | HVIHH | (SEQ. ID. NO: 19) |
| Arab. fad3 ($\Delta^{15}$) | VLGHDCGH | (SEQ. ID. NO: 5) | HRTHH | (SEQ. ID. NO: 11) | HVIHH | (SEQ. ID. NO: 19) |
| Brassica fad 3 ($\Delta^{15}$) | VLGHDCGH | (SEQ. ID. NO: 5) | HRTHH | (SEQ. ID. NO: 11) | HVIHH | (SEQ. ID. NO: 19) |
| Borage $\Delta^{12}$ (P1-81)* | VIAHECGH | (SEQ. ID. NO: 6) | HRRHH | (SEQ. ID. NO: 12) | HVAHH | (SEQ. ID. NO: 20) |
| Arab. fad2 ($\Delta^{12}$) | VIAHECGH | (SEQ. ID. NO: 6) | HRRHH | (SEQ. ID. NO: 12) | HVAHH | (SEQ. ID. NO: 20) |
| Arab. chloroplast $\Delta^{12}$ | VIGHDCAH | (SEQ. ID. NO: 7) | HDRHH | (SEQ. ID. NO: 13) | HIPHH | (SEQ. ID. NO: 21) |
| Glycine plastid $\Delta^{12}$ | VIGHDCAH | (SEQ. ID. NO: 7) | HDRHH | (SEQ. ID. NO: 13) | HIPHH | (SEQ. ID. NO: 21) |
| Spinach plastidial n-6 | VIGHDCAH | (SEQ. ID. NO: 7) | HDQHH | (SEQ. ID. NO: 14) | HIPHH | (SEQ. ID. NO: 21) |
| Synechocystis $\Delta^{12}$ | VVGHDCGH | (SEQ. ID. NO: 8) | HDHHH | (SEQ. ID. NO: 15) | HIPHH | (SEQ. ID. NO: 21) |
| Anabaena $\Delta^{12}$ | VLGHDCGH | (SEQ. ID. NO: 5) | HNHHH | (SEQ. ID. NO: 16) | HVPHH | (SEQ. ID. NO: 22) |

*P1-81 is a full length cDNA which was identified by EST analysis and shows high similarity to the Arbidopsis Δ12 desaturase (fad2)

TABLE 2

EXPRESSION OF THE BORAGE $\Delta^6$-DESATURASE IN TRANSGENIC PLANTS

| | | SEED | | | LEAF | | |
|---|---|---|---|---|---|---|---|
| PROMOTER | PLANT | GLA* RANGE | RANGE | OTA* | GLA RANGE | RANGE | OTA |
| Cauliflower mosaic virus 35S | tobacco | 1.3 | 0.7–3.1 | n.d | 20 8–11 | 19–22 | 9.7 |
| Sunflower albumin | Arabidopsis | 4.4 0.63–3.6 | 3.1–10.2 | 1.7 | n.d. | | n.d |

*mean value expressed as the percent of the $C_{18}$ fatty acids n.d. not detected

What is claimed is:

1. An isolated nucleic acid encoding an albumin 5' regulatory region which directs seed-specific expression comprising the nucleotide sequence set forth in SEQ ID NO:2.

2. An expression cassette which comprises an albumin 5' regulatory region which directs seed-specific expression, said regulatory region comprising the nucleotide sequence set forth in SEQ ID NO:2, and wherein said 5' regulatory region is operably linked to a heterologous gene or a nucleic acid encoding a sequence complementary to a native plant gene.

3. The expression cassette of claim 2 wherein the heterologous gene is at least one of a fatty acid synthesis gene or a lipid metabolism gene.

4. The expression cassette of claim 3 wherein the heterologous gene is selected from the group consisting of a lipid desaturase gene, an acyl carrier protein (ACP) gene, a thioesterase gene, an acetyl transacylase gene, an acetyl-coA carboxylase gene, a ketoacyl synthase gene, a malonyl transacylase gene and an elongase gene.

5. The expression cassette of claim 4 wherein the lipid desaturase gene is selected from the group consisting of a Δ6-desaturase gene, a Δ12-desaturase gene, and a Δ15-desaturase gene.

6. An expression vector which comprises the expression cassette of any one of claims 2–5.

7. A cell comprising the expression cassette of any one of claims 2–5.

8. A cell comprising the expression vector of claim 6.

9. The cell of claim 7 wherein said cell is a bacterial cell or a plant cell.

10. The cell of claim 8 wherein said cell is a bacterial cell or a plant cell.

11. A transgenic plant comprising the expression cassette of any one of claims 2–5.

12. A transgenic plant comprising the expression vector of claim 6.

13. A plant which has been regenerated from the plant cell of claim 9.

14. A plant which has been regenerated from the plant cell of claim 10.

15. The plant of claim 12 wherein said plant is at least one of a sunflower, soybean, maize, cotton, tobacco, peanut, oil seed rape or Arabidopisis plant.

16. The plant of claim 13 wherein said plant is at least one of a sunflower, soybean, maize, cotton, tobacco, peanut, oil seed rape or Arabidopisis plant.

17. Transgenic progeny of the plant of claim 11.

18. Transgenic progeny of the plant of claim 12.

19. Seed from the plant of claim 11.

20. Seed from the plant of claim 12.

21. A method of producing a plant with increased levels of a product of a fatty acid synthesis gene or lipid metabolism gene said method comprising:

(a) transforming a plant cell with an expression vector comprising an isolated nucleic acid encoding an albumin 5' regulatory region, said regulatory region comprising the nucleotide sequence set forth in SEQ ID NO:2, wherein said regulatory region is operably linked to at least one of an isolated nucleic acid coding for a fatty acid synthesis gene or a lipid metabolism gene; and (b) regenerating a plant with increased levels of the product of said fatty acid synthesis gene or said lipid metabolism gene from said plant cell.

22. A method of producing a plant with increased levels of gamma linolenic acid (GLA) content said method comprising:

(a) transforming a plant cell with an expression vector comprising an isolated nucleic acid encoding an albumin 5' regulatory region, said regulatory region comprising the nucleotide sequence set forth in SEQ ID NO:2, wherein said regulatory region is operably linked to a Δ6-desaturase gene; and (b) regenerating a plant with increased levels of GLA from said plant cell.

23. The method of claim 22 wherein said Δ6-desaturase gene is at least one of a cyanobacterial Δ6-desaturase gene or a borage Δ6-desaturase gene.

24. The method of claim 21 or 22 wherein said plant is a sunflower, soybean, maize, tobacco, cotton, peanut, oil seed rape or Arabidopsis plant.

25. The method of claim 21 wherein said fatty acid synthesis gene or said lipid metabolism gene is at least one of a lipid desaturase, an acyl carrier protein (ACP) gene, a thioesterase gene an elongase gene, an acetyl transacylase gene, an acetyl-coA carboxylase gene, a ketoacyl synthase gene, or a malonyl transacylase gene.

26. A method of inducing production of at least one of gamma linolenic acid (GLA) or octadecatetraeonic acid (OTA) in a plant deficient or lacking in GLA method comprising:

(a) transforming said plant with an expression vector comprising an isolated nucleic acid encoding an albumin 5' regulatory region, said regulatory region comprising the nucleotide sequence set forth in SEQ ID NO:2, wherein said regulatory region is operably linked to a Δ6-desaturase gene; and (b) regenerating a plant with increased levels of at least one of GLA or OTA.

27. A method of decreasing production of a fatty acid synthesis or lipid metabolism gene in a plant said method comprising:

(a) transforming a plant cell with an expression vector comprising an isolated nucleic acid encoding an albumin 5' regulatory region, said regulatory region comprising the nucleotide sequence set forth in SEQ ID NO:2, wherein said regulatory region is operably linked to a nucleic acid sequence complementary to a fatty acid synthesis or lipid metabolism gene; and (b) regenerating a plant with decreased production of said fatty acid synthesis or said lipid metabolism gene.

28. A method of cosuppressing a native fatty acid synthesis or lipid metabolism gene in a plant said method comprising:

(a) transforming a cell of the plant with an expression vector comprising an isolated nucleic acid encoding an albumin 5' regulatory region, said regulatory region comprising the nucleotide sequence set forth in SEQ ID NO:2, wherein said regulatory region is operably linked to a nucleic acid sequence encoding a fatty acid synthesis or lipid metabolism gene native to the plant; and (b) regenerating a plant with decreased production of said fatty acid synthesis or said lipid metabolism gene.

* * * * *

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
      (A) LENGTH: 1684 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 43..1387

(xi) SEQUENCE DESCRIPTION: SEQ ID NO:1:

```
ATATCTGCCT ACCCTCCCAA AGAGAGTAGT CATTTTTCAT CA ATG GCT GCT CAA          54
                                               Met Ala Ala Gln
                                                 1

ATC AAG AAA TAC ATT ACC TCA GAT GAA CTC AAG AAC CAC GAT AAA CCC        102
Ile Lys Lys Tyr Ile Thr Ser Asp Glu Leu Lys Asn His Asp Lys Pro
  5              10                  15                  20

GGA GAT CTA TGG ATC TCG ATT CAA GGG AAA GCC TAT GAT GTT TCG GAT        150
Gly Asp Leu Trp Ile Ser Ile Gln Gly Lys Ala Tyr Asp Val Ser Asp
              25                  30                  35

TGG GTG AAA GAC CAT CCA GGT GGC AGC TTT CCC TTG AAG AGT CTT GCT        198
Trp Val Lys Asp His Pro Gly Gly Ser Phe Pro Leu Lys Ser Leu Ala
          40                  45                  50

GGT CAA GAG GTA ACT GAT GCA TTT GTT GCA TTC CAT CCT GCC TCT ACA        246
Gly Gln Glu Val Thr Asp Ala Phe Val Ala Phe His Pro Ala Ser Thr
      55                  60                  65

TGG AAG AAT CTT GAT AAG TTT TTC ACT GGG TAT TAT CTT AAA GAT TAC        294
Trp Lys Asn Leu Asp Lys Phe Phe Thr Gly Tyr Tyr Leu Lys Asp Tyr
  70                  75                  80

TCT GTT TCT GAG GTT TCT AAA GAT TAT AGG AAG CTT GTG TTT GAG TTT        342
Ser Val Ser Glu Val Ser Lys Asp Tyr Arg Lys Leu Val Phe Glu Phe
 85                  90                  95                 100

TCT AAA ATG GGT TTG TAT GAC AAA AAA GGT CAT ATT ATG TTT GCA ACT        390
Ser Lys Met Gly Leu Tyr Asp Lys Lys Gly His Ile Met Phe Ala Thr
             105                 110                 115

TTG TGC TTT ATA GCA ATG CTG TTT GCT ATG AGT GTT TAT GGG GTT TTG        438
Leu Cys Phe Ile Ala Met Leu Phe Ala Met Ser Val Tyr Gly Val Leu
         120                 125                 130

TTT TGT GAG GGT GTT TTG GTA CAT TTG TTT TCT GGG TGT TTG ATG GGG        486
Phe Cys Glu Gly Val Leu Val His Leu Phe Ser Gly Cys Leu Met Gly
     135                 140                 145

TTT CTT TGG ATT CAG AGT GGT TGG ATT GGA CAT GAT GCT GGG CAT TAT        534
Phe Leu Trp Ile Gln Ser Gly Trp Ile Gly His Asp Ala Gly His Tyr
 150                 155                 160

ATG GTA GTG TCT GAT TCA AGG CTT AAT AAG TTT ATG GGT ATT TTT GCT        582
Met Val Val Ser Asp Ser Arg Leu Asn Lys Phe Met Gly Ile Phe Ala
165                 170                 175                 180

GCA AAT TGT CTT TCA GGA ATA AGT ATT GGT TGG TGG AAA TGG AAC CAT        630
Ala Asn Cys Leu Ser Gly Ile Ser Ile Gly Trp Trp Lys Trp Asn His
             185                 190                 195

AAT GCA CAT CAC ATT GCC TGT AAT AGC CTT GAA TAT GAC CCT GAT TTA        678
Asn Ala His His Ile Ala Cys Asn Ser Leu Glu Tyr Asp Pro Asp Leu
         200                 205                 210
```

```
CAA TAT ATA CCA TTC CTT GTT GTG TCT TCC AAG TTT TTT GGT TCA CTC         726
Gln Tyr Ile Pro Phe Leu Val Val Ser Ser Lys Phe Phe Gly Ser Leu
        215                 220                 225

ACC TCT CAT TTC TAT GAG AAA AGG TTG ACT TTT GAC TCT TTA TCA AGA         774
Thr Ser His Phe Tyr Glu Lys Arg Leu Thr Phe Asp Ser Leu Ser Arg
        230                 235                 240

TTC TTT GTA AGT TAT CAA CAT TGG ACA TTT TAC CCT ATT ATG TGT GCT         822
Phe Phe Val Ser Tyr Gln His Trp Thr Phe Tyr Pro Ile Met Cys Ala
245                 250                 255                 260

GCT AGG CTC AAT ATG TAT GTA CAA TCT CTC ATA ATG TTG TTG ACC AAG         870
Ala Arg Leu Asn Met Tyr Val Gln Ser Leu Ile Met Leu Leu Thr Lys
                265                 270                 275

AGA AAT GTG TCC TAT CGA GCT CAG GAA CTC TTG GGA TGC CTA GTG TTC         918
Arg Asn Val Ser Tyr Arg Ala Gln Glu Leu Leu Gly Cys Leu Val Phe
        280                 285                 290

TCG ATT TGG TAC CCG TTG CTT GTT TCT TGT TTG CCT AAT TGG GGT GAA         966
Ser Ile Trp Tyr Pro Leu Leu Val Ser Cys Leu Pro Asn Trp Gly Glu
        295                 300                 305

AGA ATT ATG TTT GTT ATT GCA AGT TTA TCA GTG ACT GGA ATG CAA CAA        1014
Arg Ile Met Phe Val Ile Ala Ser Leu Ser Val Thr Gly Met Gln Gln
        310                 315                 320

GTT CAG TTC TCC TTG AAC CAC TTC TCT TCA AGT GTT TAT GTT GGA AAG        1062
Val Gln Phe Ser Leu Asn His Phe Ser Ser Ser Val Tyr Val Gly Lys
325                 330                 335                 340

CCT AAA GGG AAT AAT TGG TTT GAG AAA CAA ACG GAT GGG ACA CTT GAC        1110
Pro Lys Gly Asn Asn Trp Phe Glu Lys Gln Thr Asp Gly Thr Leu Asp
                345                 350                 355

ATT TCT TGT CCT CCT TGG ATG GAT TGG TTT CAT GGT GGA TTG CAA TTC        1158
Ile Ser Cys Pro Pro Trp Met Asp Trp Phe His Gly Gly Leu Gln Phe
        360                 365                 370

CAA ATT GAG CAT CAT TTG TTT CCC AAG ATG CCT AGA TGC AAC CTT AGG        1206
Gln Ile Glu His His Leu Phe Pro Lys Met Pro Arg Cys Asn Leu Arg
        375                 380                 385

AAA ATC TCG CCC TAC GTG ATC GAG TTA TGC AAG AAA CAT AAT TTG CCT        1254
Lys Ile Ser Pro Tyr Val Ile Glu Leu Cys Lys Lys His Asn Leu Pro
390                 395                 400

TAC AAT TAT GCA TCT TTC TCC AAG GCC AAT GAA ATG ACA CTC AGA ACA        1302
Tyr Asn Tyr Ala Ser Phe Ser Lys Ala Asn Glu Met Thr Leu Arg Thr
405                 410                 415                 420

TTG AGG AAC ACA GCA TTG CAG GCT AGG GAT ATA ACC AAG CCG CTC CCG        1350
Leu Arg Asn Thr Ala Leu Gln Ala Arg Asp Ile Thr Lys Pro Leu Pro
                425                 430                 435

AAG AAT TTG GTA TGG GAA GCT CTT CAC ACT CAT GGT T AAAATTACCC           1397
Lys Asn Leu Val Trp Glu Ala Leu His Thr His Gly
                440                 445

TTAGTTCATG TAATAATTTG AGATTATGTA TCTCCTATGT TTGTGTCTTG TCTTGGTTCT      1457

ACTTGTTGGA GTCATTGCAA CTTGTCTTTT ATGGTTTATT AGATGTTTTT TAATATATTT      1517

TAGAGGTTTT GCTTTCATCT CCATTATTGA TGAATAAGGA GTTGCATATT GTCAATTGTT      1577

GTGCTCAATA TCTGATATTT TGGAATGTAC TTTGTACCAC GTGGTTTTCA GTTGAAGCTC      1637

ATGTGTACTT CTATAGACTT TGTTTAAATG GTTATGTCAT GTTATTT                    1684

(2) INFORMATION FOR SEQ ID NO:2:

(i) SEQUENCE CHARACTERISTICS:
        (A) LENGTH: 843 base pairs
        (B) TYPE: nucleic acid
        (C) STRANDEDNESS: double
        (D) TOPOLOGY: linear (ii) MOLECULE TYPE: DNA (genomic)
```

(xi) SEQUENCE DESCRIPTION: SEQ ID NO:2:

```
GAATTCTATC ACTAGTGACC ACCCCATCCC CTTATTTCAA TAATGGAACA CAAAAAAATT      60
TTAAAAAATA GTTGCTGTTA ATTGTTTAAC CGTCATTTTC CAACATTACT AGCTAATCGT     120
TAATTGATCT TCATAAAAAA AAAAATTGCT ATGGGTACTA TTGAGATTGT ATATCTTATC     180
AGTTAGGCCT AAGGGGGGGG TCAGTGATAT TACGAATGAT ACAAACATCA ACGCGTGGAA     240
CATTACAAAA TTCCGTAATT TTTTCAACGC CGTGATGGTT TTTTTTTTTT TTTTTTTTTT     300
TGATGGTAAT TGTTGGTTGG GGGGAAATTA TTGGGTATGG TGTTGAGTAT GACCACCCCC     360
ACTAAAAAAG GTTGTGAGTG ATGTAAAAAT GGTTGCTGAC ATGACGAAAC ATAATTGGAT     420
ATTGTGAGTG ATAAAATTTT ATCATTAGTG ACCACCCCGC CTCCCCTTAT CATATGTTGT     480
TATCTTCCAT AGTTGCGGTA TACCAACATA TGGTAGTTTT TATATTTATA GTTTATATTT     540
TCATTAAACT CTCTTCGCCA GGCTACTTGT ATTGTAATCA TATGGAATCT CAACTCCAGT     600
TGGAGCCATT CCATCATATA TTTCCATTTC CAAACAAAGA GAATTGACAC CTCATACATA     660
CTCCAAAGCA TACTTCCACT TGCTATAATT TTCATGTAAA AACTCGTACG TGTTATTCGA     720
CAATGTTCAT ATAACGCCAC CGATTAAACT CACCTCTCCA CGTATGAACC TCCACCCACC     780
ATATATACGC ACCACCACCA CACCATAATT CACACAACCA CAACACCATC TCCCACAGGA     840
TCC                                                                   843
```

(2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Trp Ile Gly His Asp Ala Gly His
1               5

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Asn Val Gly His Asp Ala Asn His
1               5

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Val Leu Gly His Asp Cys Gly His
1               5

(2) INFORMATION FOR SEQ ID NO:6:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Val Ile Ala His Glu Cys Gly His
1               5
```

(2) INFORMATION FOR SEQ ID NO:7:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Val Ile Gly His Asp Cys Ala His
1               5
```

(2) INFORMATION FOR SEQ ID NO:8:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Val Val Gly His Asp Cys Gly His
1               5
```

(2) INFORMATION FOR SEQ ID NO:9:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
His Asn Ala His His
1               5
```

(2) INFORMATION FOR SEQ ID NO:10:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
His Asn Tyr Leu His His
1               5
```

(2) INFORMATION FOR SEQ ID NO:11:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

His Arg Thr His His
1               5

(2) INFORMATION FOR SEQ ID NO:12:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

His Arg Arg His His
1               5

(2) INFORMATION FOR SEQ ID NO:13:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

His Asp Arg His His
1               5

(2) INFORMATION FOR SEQ ID NO:14:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

His Asp Gln His His
1               5

(2) INFORMATION FOR SEQ ID NO:15:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

His Asp His His His
1               5

(2) INFORMATION FOR SEQ ID NO:16:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

His Asn His His His
1         5

(2) INFORMATION FOR SEQ ID NO:17:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

Phe Gln Ile Glu His His
1         5

(2) INFORMATION FOR SEQ ID NO:18:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

His Gln Val Thr His His
1         5

(2) INFORMATION FOR SEQ ID NO:19:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:19:

His Gln Val Thr His His
1         5

(2) INFORMATION FOR SEQ ID NO:20:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

His Val Ala His His
1         5

(2) INFORMATION FOR SEQ ID NO:21:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

His Ile Pro His His
1             5

(2) INFORMATION FOR SEQ ID NO:22:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:22:

His Val Pro His His
1             5